US006996853B2

(12) United States Patent
Gabriel

(10) Patent No.: US 6,996,853 B2
(45) Date of Patent: Feb. 14, 2006

(54) HAIR FRESHENING DEVICE

(76) Inventor: Candace Gabriel, 13410 Kingsbury Dr., Carmel, IN (US) 46032

( * ) Notice: Subject to any disclaimer, the term of this patent is extended or adjusted under 35 U.S.C. 154(b) by 200 days.

(21) Appl. No.: 10/463,709

(22) Filed: Jun. 17, 2003

(65) Prior Publication Data

US 2004/0255363 A1 Dec. 23, 2004

(51) Int. Cl.
*A42B 1/18* (2006.01)
(52) U.S. Cl. .......................... 2/174; 2/171.2
(58) Field of Classification Search ............. 2/174, 2/209.1, 3, 171.2; 206/0.5; 132/212, 273, 132/275; 239/36; 424/401–404, 422, 443, 424/444, 70.1, 69, 70.8
See application file for complete search history.

(56) References Cited

U.S. PATENT DOCUMENTS

| 649,826 | A | * | 5/1900 | Eldred ........................ 2/171.2 |
| 935,832 | A | | 10/1909 | Barnes |
| 1,051,149 | A | * | 1/1913 | McLeod ....................... 239/36 |
| 4,296,763 | A | * | 10/1981 | Priest et al. ................. 132/200 |
| 4,343,783 | A | | 8/1982 | Hooper et al. |
| 4,465,232 | A | * | 8/1984 | Field ........................... 239/36 |
| 4,744,514 | A | * | 5/1988 | Gadoua ........................ 239/36 |
| 5,566,395 | A | | 10/1996 | Nebeker |
| 5,823,432 | A | * | 10/1998 | Hogan ......................... 239/36 |
| 5,823,598 | A | * | 10/1998 | Clare et al. ................. 296/37.6 |
| 5,826,598 | A | * | 10/1998 | Meehan ...................... 132/275 |
| 6,167,574 | B1 | | 1/2001 | Hayashida |
| 6,237,154 | B1 | | 5/2001 | Reuven |
| 6,351,852 | B1 | | 3/2002 | Propp |
| 6,820,283 | B2 | * | 11/2004 | Graneto, III ................ 2/171.2 |
| 2001/0055540 | A1 | | 12/2001 | Bonamarte |
| 2002/0110583 | A1 | | 8/2002 | Grey |
| 2002/0131943 | A1 | | 9/2002 | Grey |
| 2003/0059459 | A1 | * | 3/2003 | Pyles ......................... 424/443 |

FOREIGN PATENT DOCUMENTS

GB 2343627 * 5/2000

* cited by examiner

*Primary Examiner*—Katherine M. Moran
(74) *Attorney, Agent, or Firm*—Baker & Daniels LLP

(57) ABSTRACT

The present invention provides a hair freshening apparatus that includes a hair retaining device having a compartment with a fragrance-permeable side adapted to lie adjacent the hair; and a freshening element disposed within the compartment and impregnated with a freshening substance. The compartment of the hair freshening device may include an opening, such that the freshening element may be removably disposed within the compartment through the opening. The compartment may also include a fastening means for closing the opening and thereby retaining the freshening element within the compartment. The compartment of the hair freshening device may also be removably attached to the hair retaining device by a fastener. The freshening substance may be a scented fragrance or an odor neutralizing agent. The hair retaining device may be a shower cap having a water-impermeable outer surface. Alternatively, hair retaining device may be a hair net, hair cap, or hat.

19 Claims, 5 Drawing Sheets

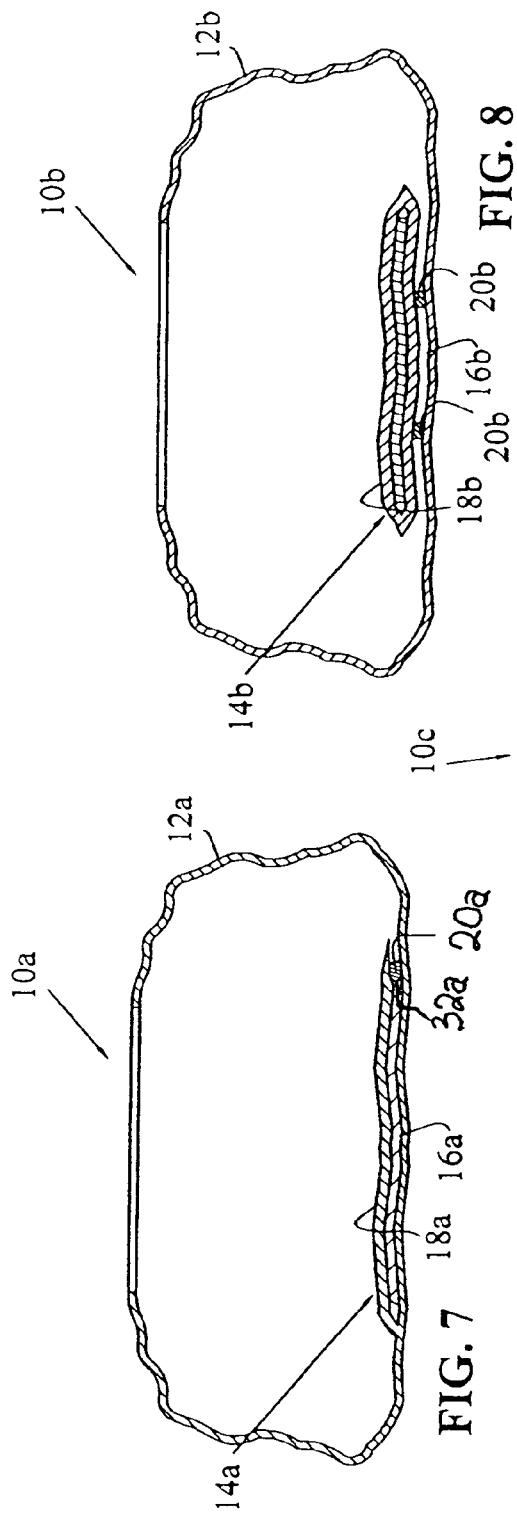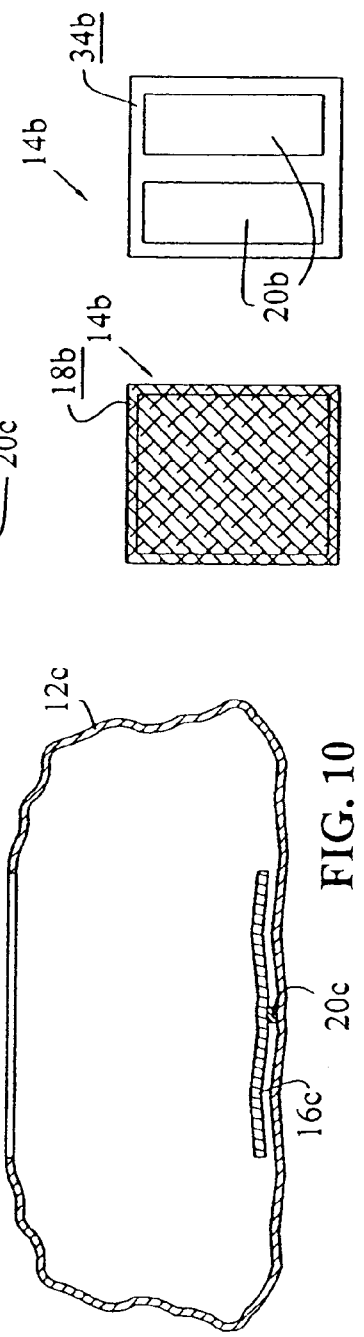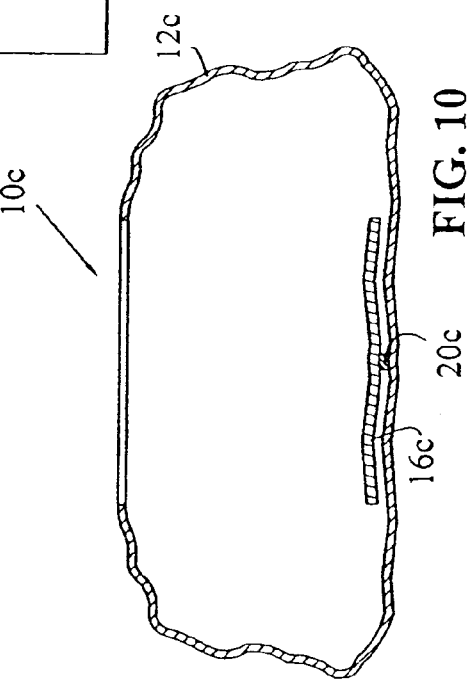

HAIR FRESHENING DEVICE

BACKGROUND OF THE INVENTION

1. Field of the Invention

The present invention relates to bath and beauty aids, particularly, hair accessories and treatments.

2. Description of the Related Art

It is generally known that hair readily absorbs odors, especially smoke and cooking odors. This phenomenon has driven many people to wash their hair daily. However, this daily ritual strips the hair of its natural conditioning oils, which over time can cause the hair to become dull, dry and brittle. Moreover, this daily cleansing ritual is often followed by blow drying and styling the hair with heat, which can further strip and damage the hair. To prevent excessive damage to the hair caused by daily cleansing, drying and styling, it is recommended that the hair be washed every other day, a few times a week, or even once a week. However, many people are reluctant to follow this advice because the odors absorbed by the hair remain and can often be unpleasant and embarrassing. Therefore, a need exists for a device that freshens the hair without cleansing, drying or styling.

SUMMARY OF THE INVENTION

The present invention provides a hair freshening apparatus that includes a hair retaining device having an associated compartment with a fragrance-permeable side located next to the interior portion of the hair retaining device; and a freshening element disposed within the compartment and impregnated with a freshening substance. The compartment of the hair freshening device may include an opening, such that the freshening element may be removably disposed within the compartment through the opening. The compartment may also include a closure device for closing the opening and thereby retaining the freshening element within the compartment. The compartment of the hair freshening device may also be removably attached to the hair retaining device by a fastener. The freshening substance may be a scented fragrance or an odor neutralizing agent. The hair retaining device may be a shower cap having a water-impermeable outer surface, such that the user can wear the apparatus while showering. Alternatively, hair retaining device may be a hair net or hair cap that can retain the hair.

The present invention also provides a hair freshening device including a hair retaining device made of a bag-like material defining an interior surface and an exterior surface; and including a non-fluidous freshening layer positioned adjacent the interior surface and impregnated with a freshening substance.

The embodiment disclosed below is not intended to be exhaustive or limit the invention to the precise form disclosed in the following detailed description. Rather, the embodiment is chosen and described so that others skilled in the art may utilize its teachings.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein:

FIG. 7 is a sectional view of a hair freshening apparatus in accordance with another embodiment of the present invention;

FIG. 8 is a sectional view of a hair freshening apparatus according to another embodiment of the present invention;

FIGS. 9A and 9B are bottom and top views, respectively, of the compartment of the hair freshening apparatus of FIG. 8;

FIG. 10 is a hair freshening apparatus in accordance with another embodiment of the present invention;

FIG. 11 is a top view of the freshening element of the hair freshening apparatus of FIG. 10.

DETAILED DESCRIPTION

The embodiments hereinafter disclosed are not intended to be exhaustive or limit the invention to the precise forms disclosed in the following description. Rather the embodiments are chosen and described so that others skilled in the art may utilize its teachings.

Figure 2:
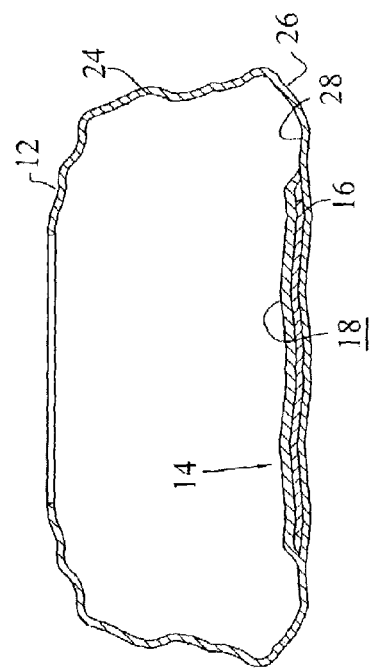
FIG. 2 is a sectional view of the hair freshening apparatus of FIG. 1 taken along lines 2—2.
Figure 1:
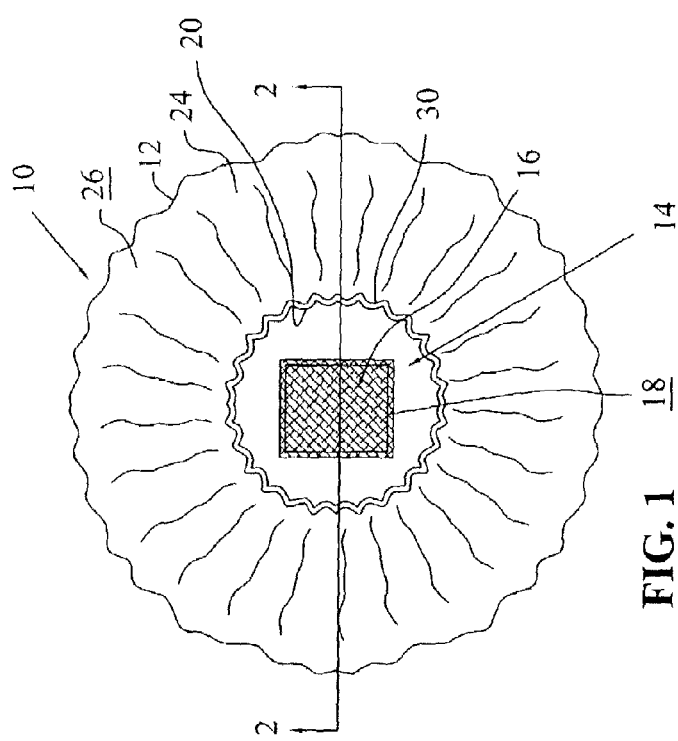
FIG. 1 is a bottom view of a hair freshening apparatus in accordance with one embodiment of the present invention.
Figure 4:
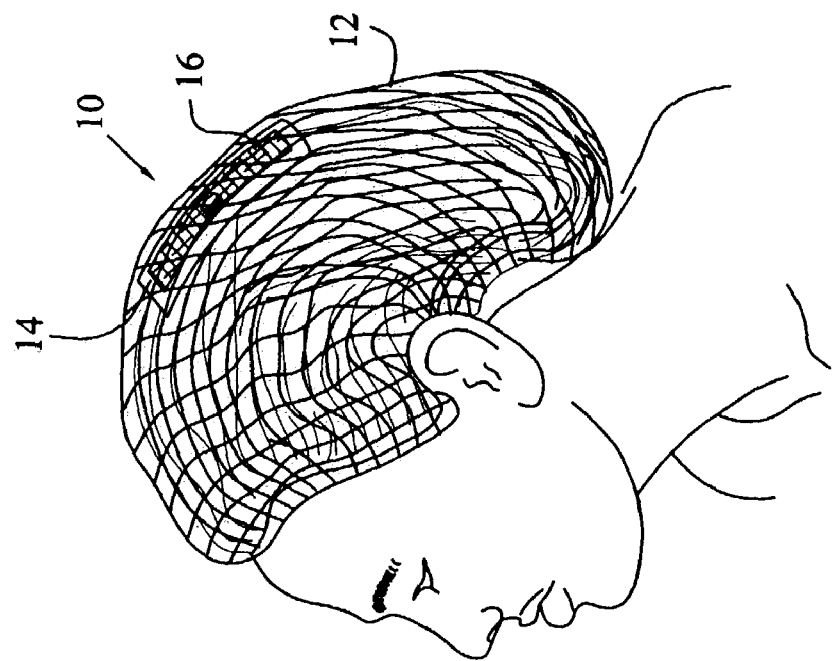
FIG. 4 is a perspective view of another embodiment of the present invention positioned on a user's head.
Figure 3:
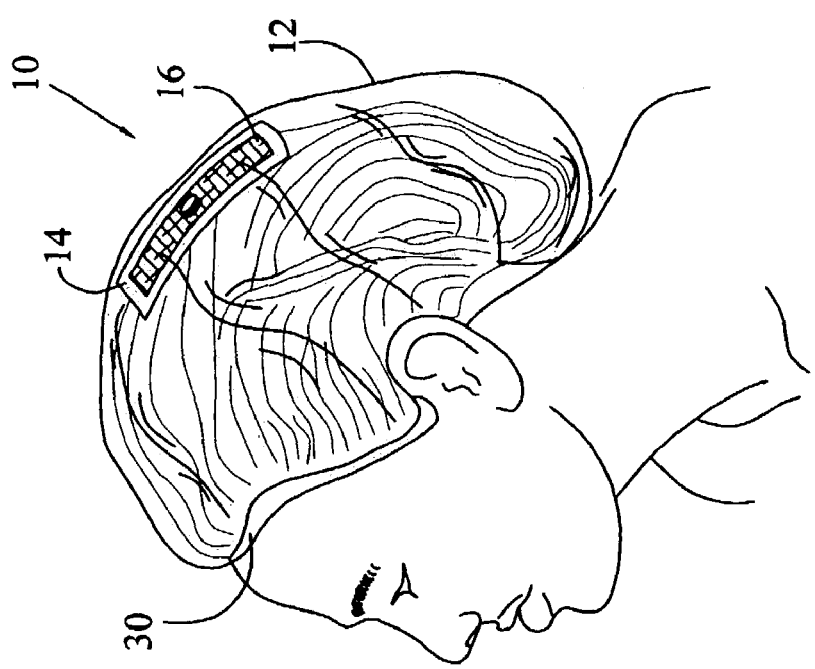
FIG. 3 is a perspective view of the apparatus of FIG. 1 positioned on a user's head.

FIGS. 1–6 illustrate hair freshening apparatus 10 in accordance with the present invention. Hair freshening apparatus 10, generally, includes hair retaining device 12 having compartment 14, and freshening element 16 disposed within compartment 14. Referring to FIGS. 1–3, hair retaining device 12 may be similar to a shower cap and includes a layer of material 24 arranged in a bag-like configuration. Material 24 includes inner surface 28 and outer surface 26. Hair retaining device 12 may be made of a vinyl or plastic such that outer surface 26 is impervious to water. Alternatively, hair retaining device 12 may be made of a paper, similar to a surgical cap, thereby providing an inexpensive, disposable option. Hair retaining device 12 may also be made of cotton, nylon, rubber or any other material capable of retaining the hair. Material 24 includes opening 22, which may be bordered by elastic 30 or by a draw string (not shown). Opening 22 is configured to receive a portion of the user's head and/or hair, while elastic 30 snuggly grips the user's head to seat hair retaining device 12 over user's head and hair.

Figure 6:
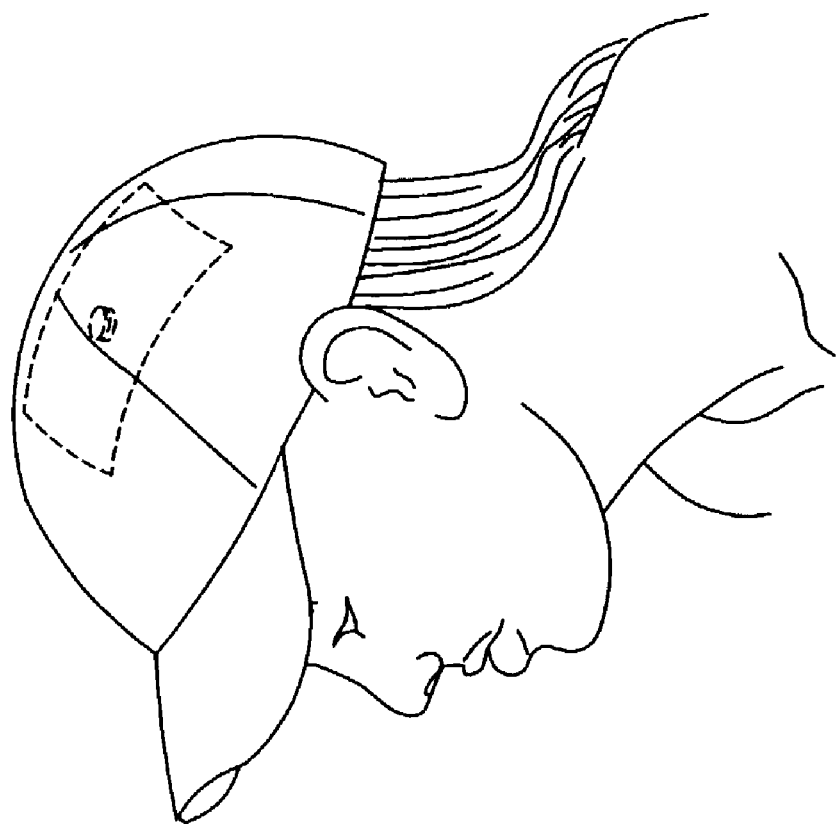
FIG. 6 is a perspective view of another embodiment of the present invention positioned on a user's head.
Figure 5:
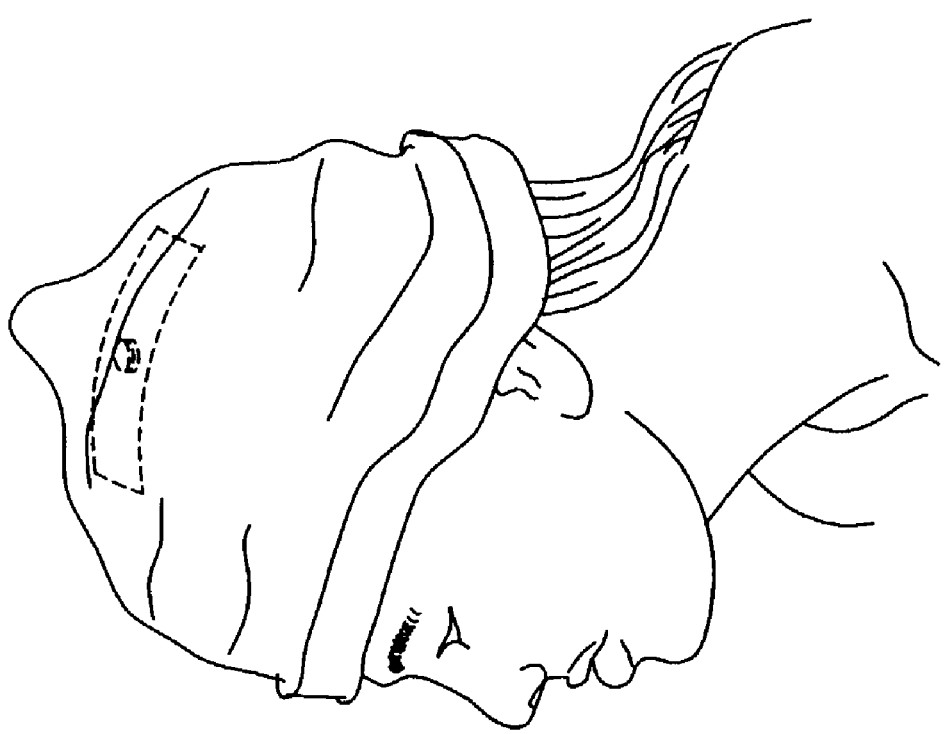
FIG. 5 is a perspective view of another embodiment of the present invention positioned on a user's head.

Although FIGS. 1–3 show a hair retaining device having only a single layer, the hair retaining device may be comprised of multiple layers of material. Furthermore, the hair retaining device need not be a standard shower cap, other suitable hair retaining devices such as a hair net, shown in FIG. 4; a knit cap, shown in FIG. 5; or a hat, shown in FIG. 6 are within the scope of the invention.

Referring again to FIGS. 1–2, compartment 14 is affixed to inner surface 28 of hair retaining device 12 and includes fragrance-permeable side 18, which lies adjacent to the hair when hair retaining device 12 is worn by the user. Fragrance-permeable side 18 may be made of netting, mesh, loose knit fabric, perforated plastic or fabric, or any other material through which a fragrance or odor neutralizing compound may permeate. Compartment 14 may be affixed to hair retaining device using adhesive, heat sealing or any other known methods of fixation. Alternatively, compartment 14 may be integrally formed with inner surface 28 of hair retaining device 12.

Freshening element 16 is disposed within compartment 14 and is impregnated with a freshening substance, such as a fragrance or an odor neutralizing agent. For instance, the freshening substance may be one or more scented oils having floral or plant scents, such as lilac, gardenia, or juniper. Alternatively, the freshening substance may be the user's favorite perfume. Some users may not like perfumes and fragrances, or may be sensitive to such fragrances. In this case, fragrance-free odor neutralizing agents, such as baking soda or cyclodextrins (a component found in odor-neutralizing agents), may be employed as the freshening substance.

Freshening element 16 may be made of any material capable of being impregnated with a fragrance or odor neutralizing agent. Such materials may include paper, cardboard, cloth, potpourri, and/or plastic. As shown in FIGS. 1–2, freshening element 16 is substantially flat or laminar and is rectangular in shape. However, freshening element 16 may be any shape, size or thickness compatible with compartment 14. A flat, laminar freshening element may be particularly useful with smaller, tighter-fitting hair retaining devices, which cannot accommodate larger, heavier freshening elements. For instance, a laminar, lightweight freshening element may be used with a hair net retaining device, which might not accommodate a heavy freshening element. Likewise, a flexible laminar freshening element may be used with a tighter fitting knit cap type of hair retaining device so as not to interfere with the fit of the hair retaining device.

In use, the user places her head and hair within opening 22 and positions elastic 30 at the desired location, for example around the hair line, as shown in FIG. 3. The user then wears apparatus 10 thus allowing the freshening substance from freshening element 16 to permeate through the fragrance-permeable side 18 of compartment 14 and to the hair. For instance, the user may wear hair freshening apparatus 10 to bed at night, or may wear hair freshening apparatus 10 during showering. Apparatus 10 of FIGS. 1–3 may include water impervious outer surface 26 that prevents the hair from getting wet during bathing, thereby allowing the user to wear apparatus 10 in the shower and offering the user added convenience. Hair freshening apparatus 10 may also be disposable such that the user may dispose of hair freshening apparatus 10 when the freshening element no longer emits freshening substance.

Referring now to FIG. 7, an alternative embodiment is shown. Hair freshening apparatus 10a includes hair retaining device 12a, compartment 14a, and freshening element 16a. Compartment 14a includes a fragrance-permeable side 18a through which the freshening substance of freshening element 16a may permeate. Compartment 14a includes opening 32a through which hair freshening element 16a may be removably inserted into compartment 14a. Opening 32a may be closed by fastener 20a which may be any suitable fastener, such as a button, snap, zipper, hook and loop, or other fasteners. Alternatively, opening 32a may be bordered with elastic such that opening is self-closing. In other word, the elastic would bias the opening to a gathered position effectively closing the opening. This particular embodiment provides versatility by allowing the user to alternate freshening elements having different freshening substances. For instance, the user may decide to use a floral scent one day and switch to a citrus blend or odor neutralizing compound on another day. In addition, hair freshening apparatus 10a need not be disposed of when the freshening substance of freshening element 16a loses its effectiveness. Instead, the user may remove freshening element 16a and replace it with a new element, or may replenish the original freshening element by applying additional freshening substance.

FIGS. 8 and 9A–B show yet another embodiment, wherein hair freshening apparatus 10b includes hair retaining device 12b, compartment 14b, and freshening element 16b disposed within compartment 14b. As shown in FIG. 9A, compartment 14b includes fragrance-permeable side 18b through which the freshening substance from element 16b can permeate. Opposite fragrance-permeable side 18b is mounting side 34b, as illustrated in FIG. 9B. Mounting side 34b includes fasteners 20b, which may be strips of hook and loop fasteners, tape, adhesive, snaps, or other fasteners. Fasteners 20b connect compartment 14b to hair retaining device 12b. This embodiment provides versatility by allowing the user to replace compartment 14b with a compartment having a new or fresh scent.

Referring now to FIGS. 10 and 11, hair freshening apparatus 10c includes freshening element 16c, which may be removably mounted directly to hair retaining device 12c by fastener 20c. In this case, freshening element 16c is made of a rigid material, such as cardboard or plastic, and includes fastener 20c that directly engages hair retaining device 12c.

Figure 12:
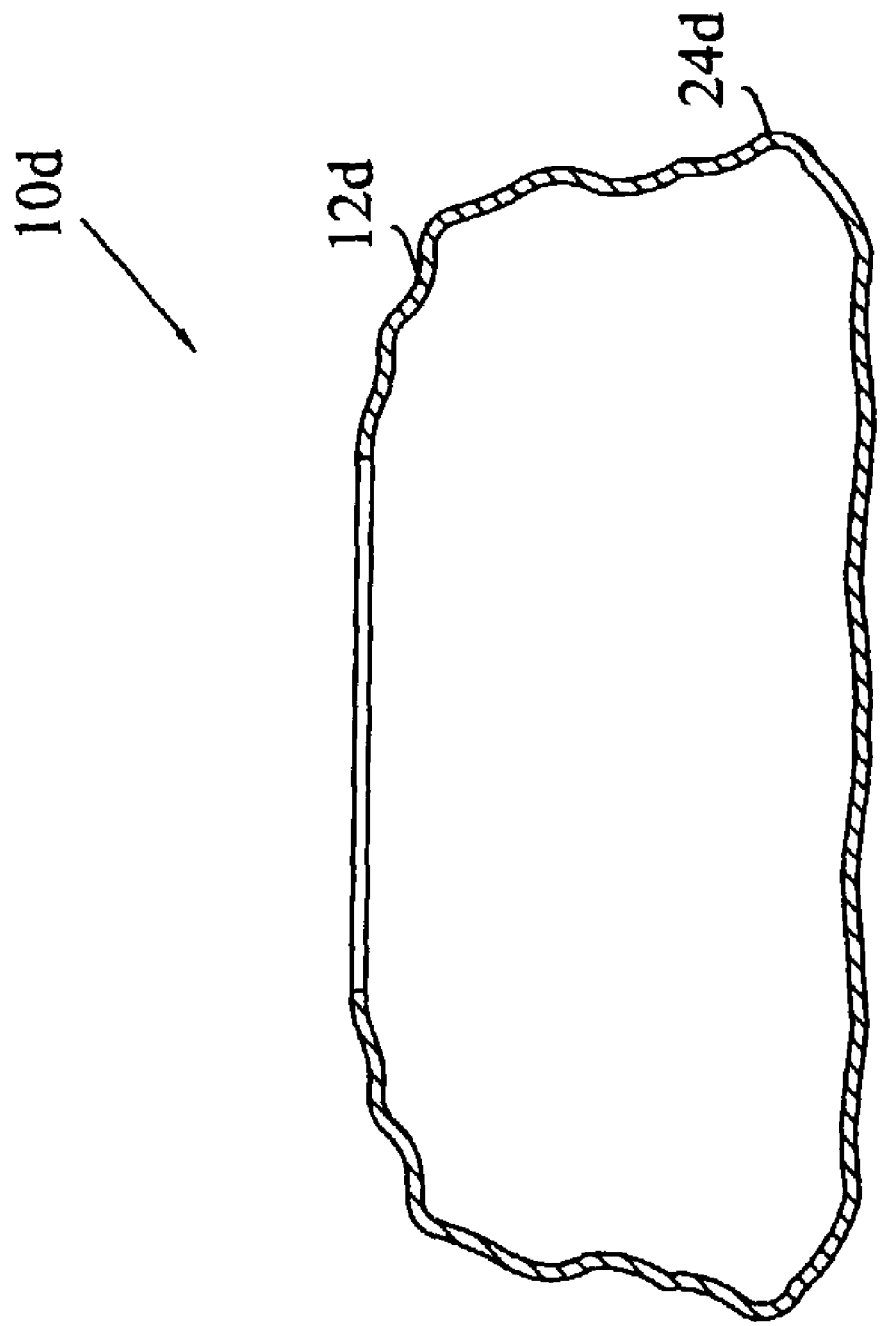
FIG. 12 is a sectional view of a hair freshening apparatus according to another embodiment of the present invention.

In yet another embodiment shown in FIG. 12, hair freshening apparatus 10d may simply include hair retaining device 12d wherein the material 24d, itself, is impregnated with a freshening substance, such as a fragrance or an odor-neutralizing compound. For example, material 24d may be a scented-plastic, a scented cloth, a scented paper, or other scented webbing material. Or, in the case of multi-layer hair retaining devices, a layer of the hair retaining device may be impregnated with a freshening substance. Such embodiments would be ideal for use in an environment where disposable hair retaining devices are used, such as hospitals, kitchens, restaurants, spas and/or hotels.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A hair freshening device comprising:
a shower cap having an inner surface and a water impermeable outer surface; said shower cap defining an interior portion adapted to contain and cover the hair;
a compartment coupled to said inner surface of said shower cap, said compartment having a fragrance-permeable side located proximate to said interior portion of said shower cap; and
a freshening element disposed within said compartment, said freshening element impregnated with a freshening substance.

2. The hair freshening device of claim 1 wherein said compartment includes an opening and said freshening element is removably disposed within said compartment through said opening.

3. The hair freshening device of claim 2 wherein said opening of said compartment includes a fastener for closing said opening and thereby retaining said freshening element within said compartment.

4. The hair freshening device of claim 3 wherein said fastener is a snap.

5. The hair freshening device of claim 3 wherein said fastener is a hook and loop fastener.

6. The hair freshening device of claim 1 further comprising a compartment fastener removably fixing said compartment to said hair retaining device.

7. The hair freshening device of claim 1 wherein said freshening element comprises a cloth material.

8. The hair freshening device of claim 1 wherein said freshening element comprises a paper material.

9. The hair freshening device of claim 1 wherein said freshening element comprises a plastic material.

10. The hair freshening device of claim 1 wherein said freshening substance is a scented fragrance, said scented fragrance capable of permeating said fragrance-permeable side of said compartment.

11. The hair freshening device of claim 1 wherein said freshening substance is an odor neutralizing agent, said odor neutralizing agent capable of permeating said fragrance-permeable side of said compartment.

12. A device for freshening the hair on a person's head, the device comprising:
   a hair retaining device including a bag-like material defining an interior portion for retaining and enveloping the hair, said material including an opening in communication with said interior portion for receiving the hair, said opening bordered by a gripping structure adapted to grip the head; and
   a freshening element removably attached to said material of said hair retaining device, said freshening element impregnated with a freshening substance, wherein said bag-like material includes a water-impermeable outer surface.

13. A device for freshening the hair on a person's head, the device comprising:
   a hair retaining device including a bag-like material defining an interior portion for retaining and enveloping the hair, said material including an opening in communication with said interior portion for receiving the hair, said opening bordered by a gripping structure adapted to grip the head; and
   a freshening element removably attached to said material of said hair retaining device, said freshening element impregnated with a freshening substance, wherein said bag-like material comprises a netting material.

14. A device for freshening the hair on a person's head, the device comprising:
   a hair retaining device including a bag-like material defining an interior portion for retaining and enveloping the hair, said material including an opening in communication with said interior portion for receiving the hair, said opening bordered by a gripping structure adapted to grip the head; and
   a freshening element removably attached to said material of said hair retaining device, said freshening element impregnated with a freshening substance, wherein said bag-like material comprises a paper material.

15. The hair freshening device of claim 14 further comprising a fastener, said fastener removably attaching said freshening element to said interior surface.

16. The hair freshening device of claim 14 wherein said freshening substance is a scented fragrance.

17. The hair freshening device of claim 14 wherein said freshening substance is an odor neutralizing agent.

18. The hair freshening device of claim 14 further comprising a compartment coupled to an inner surface of said material, said compartment having a fragrance-permeable side located proximate to said interior portion, said compartment having a compartment opening, said freshening element removably disposed within said compartment through said compartment opening.

19. The hair freshening device of claim 18 wherein said compartment includes a fastener, said fastener closing said compartment opening.

* * * * *